United States Patent
Vanney et al.

(10) Patent No.: US 6,237,607 B1
(45) Date of Patent: *May 29, 2001

(54) TRANSMYOCARDIAL IMPLANT PROCEDURE

(75) Inventors: Guy P. Vanney, Blaine; Thomas L. Odland, Lino Lakes; Eric E. Solien, New Brighton, all of MN (US)

(73) Assignee: HeartStent Corporation, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/433,454

(22) Filed: Nov. 4, 1999

Related U.S. Application Data

(63) Continuation of application No. 09/063,160, filed on Apr. 20, 1998, now Pat. No. 6,029,672.

(51) Int. Cl.$^7$ ................................................ A61B 19/00
(52) U.S. Cl. ................................................ 128/898; 604/8
(58) Field of Search .................................. 128/898, 897; 623/1.1, 1.23, 11.11, 23.64, 66; 604/8; 606/194

(56) References Cited

U.S. PATENT DOCUMENTS

| 5,409,019 | 4/1995 | Wilk . |
| 5,655,548 | 8/1997 | Nelson et al. . |
| 5,755,682 | 5/1998 | Knudson et al. . |
| 5,807,384 | 9/1998 | Mueller . |
| 5,810,836 | 9/1998 | Hussein et al. . |

FOREIGN PATENT DOCUMENTS

| 2 316 322 | 2/1998 | (GB) . |
| WO 98/06356 | 2/1998 | (WO) . |
| WO 98/08456 | 3/1998 | (WO) . |
| WO 98/46115 | 10/1998 | (WO) . |
| WO 99/17683 | 4/1999 | (WO) . |

OTHER PUBLICATIONS

Goldman, Alfred, et al., "Experimental methods for producing a collateral circulation to the heart directly form the left ventricle", *J. Thoracic Surg.*, 31(3):364–374, (Mar. 1956).

Munro, I. et al., "Mycocardial revascularization by a new method of carrying blood directly from the left ventricle cavity inot the coronary circulation", *J. Thoracic Surg.*, 34(2):257–264, (Jul. 1969).

*Primary Examiner*—Dinh X. Nguyen
(74) *Attorney, Agent, or Firm*—Merchant & Gould P.C.

(57) ABSTRACT

A blood flow path is formed from a heart chamber to a coronary vessel on an exterior surface of a heart wall. A hollow conduit has a vessel portion and a myocardial portion. The vessel portion has an open leading end sized to be inserted into the coronary vessel. The myocardial portion has an open leading end and the myocardium portion is sized to extend through a thickness of the heart wall. The myocardial portion is placed in the heart wall with the open leading end of the myocardial portion protruding into the heart chamber. Blood flow through the conduit from the heart chamber is at least partially blocked. The leading end of the vessel portion is placed in the coronary vessel. Blood flow through the conduit from the heart chamber and into the vessel is then opened.

17 Claims, 12 Drawing Sheets

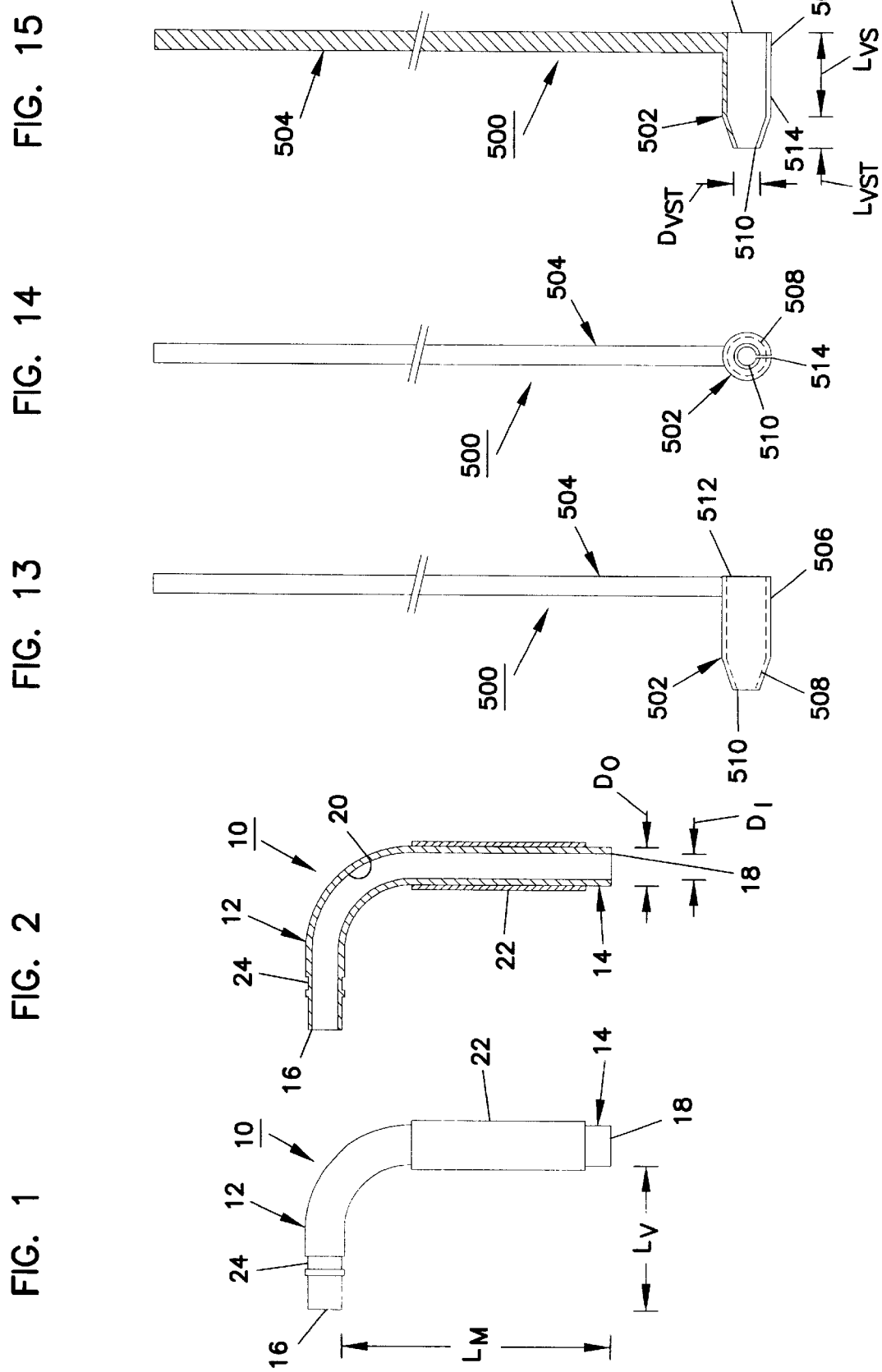

FIG. 10 FIG. 11 FIG. 12
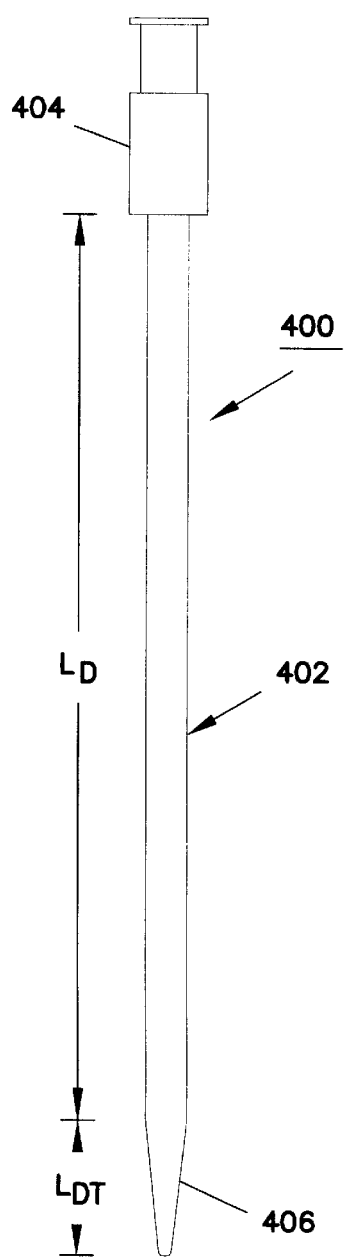
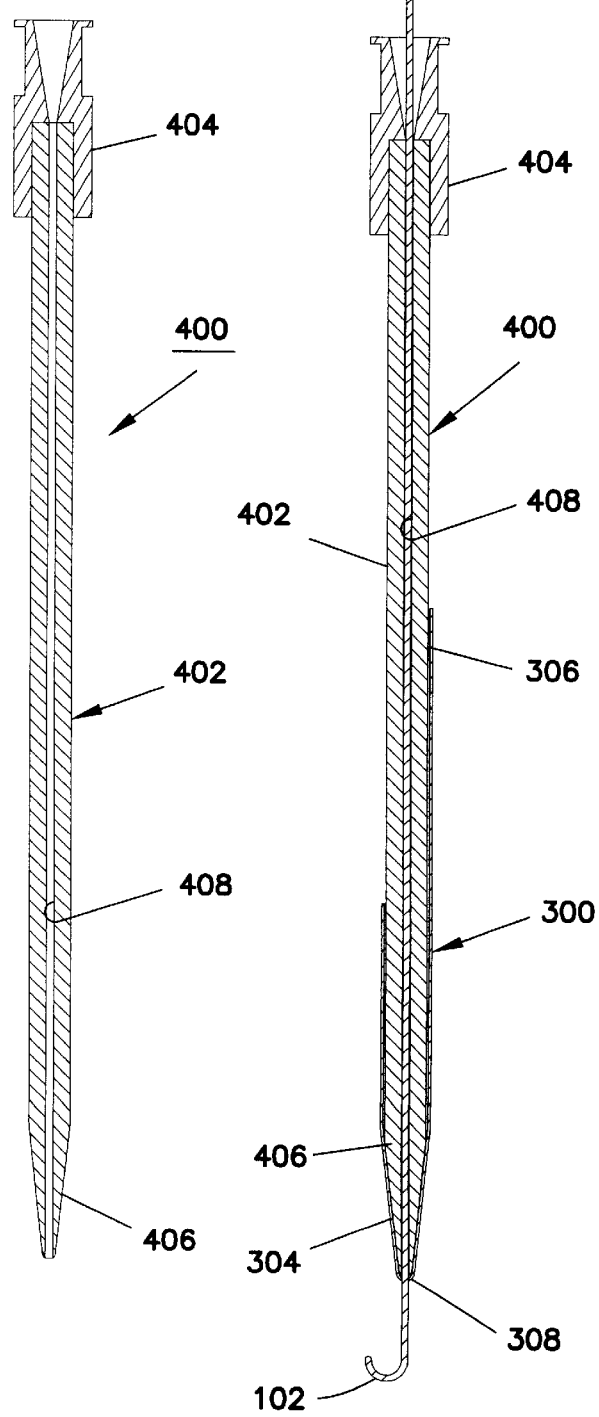

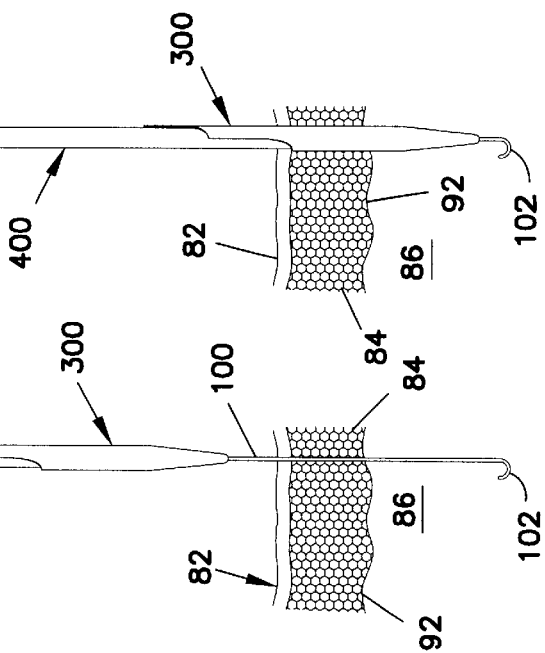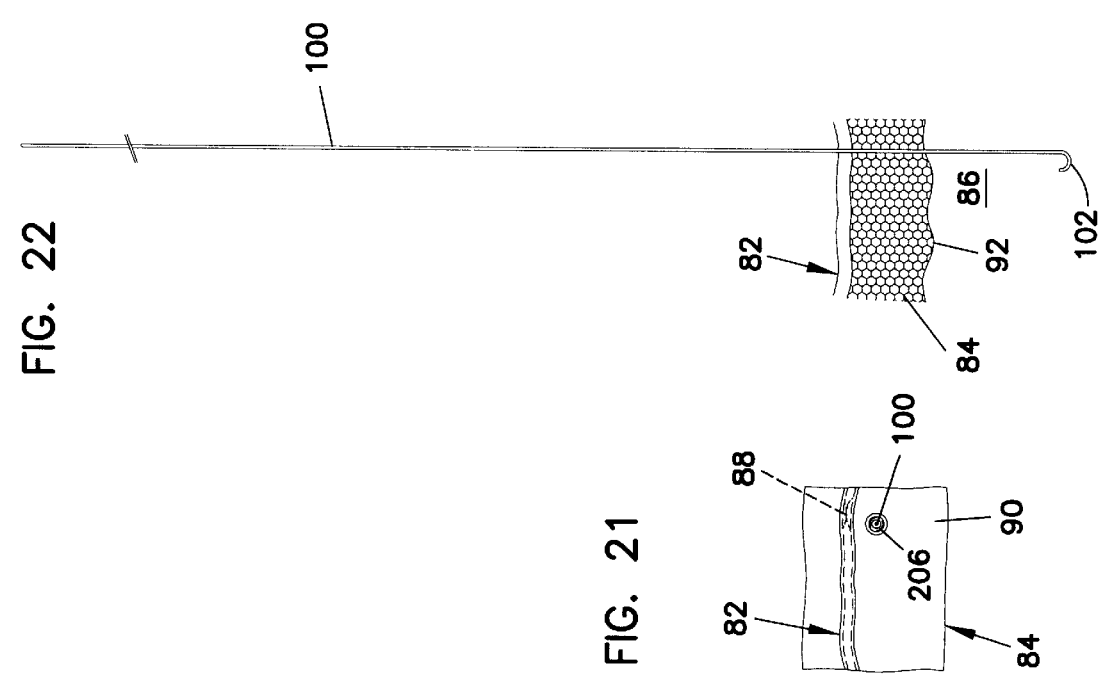

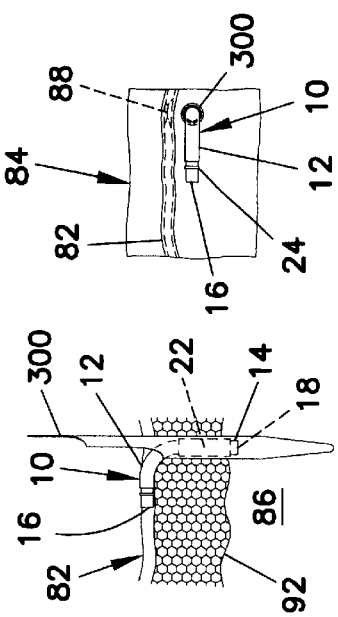
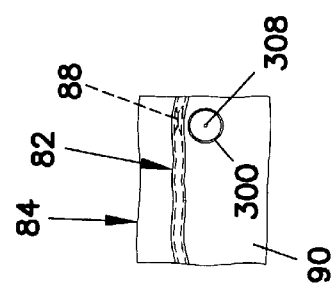
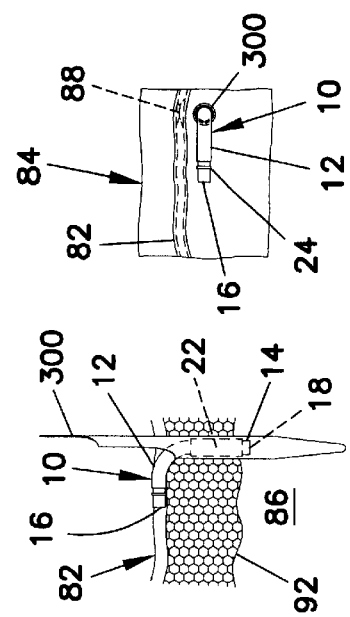
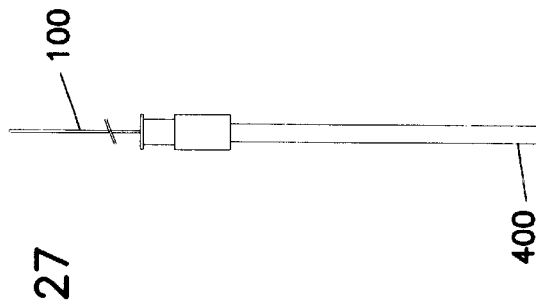
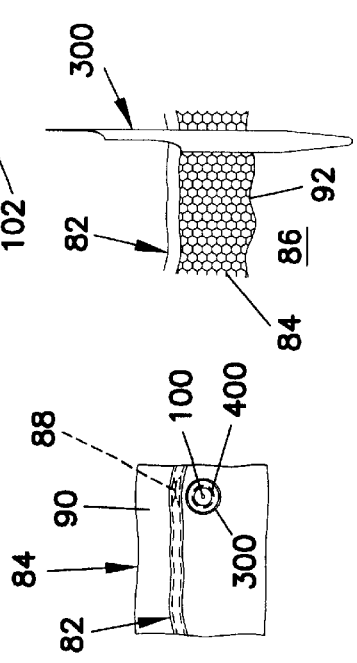

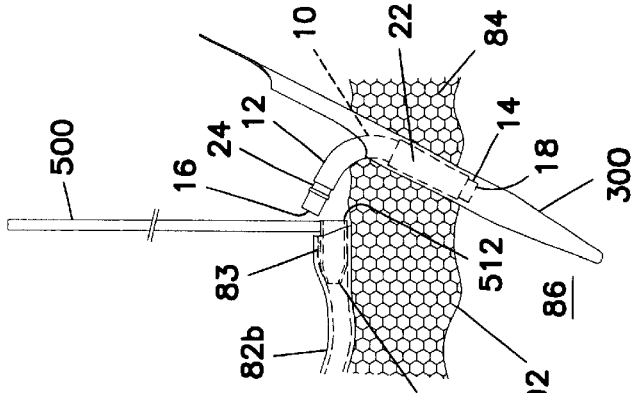
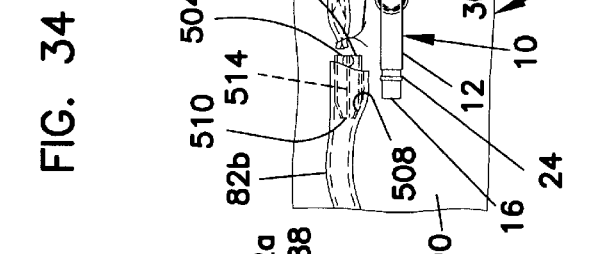
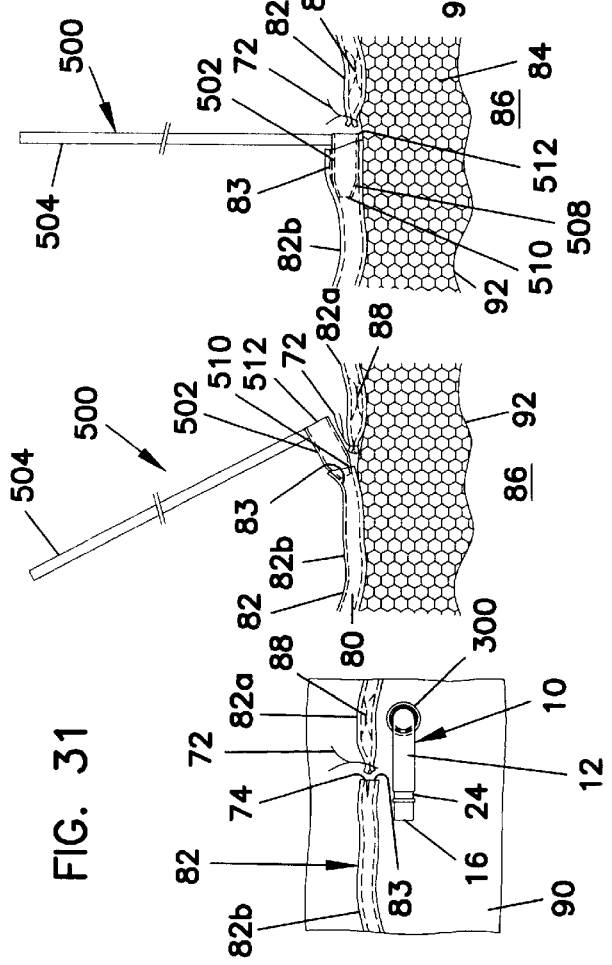

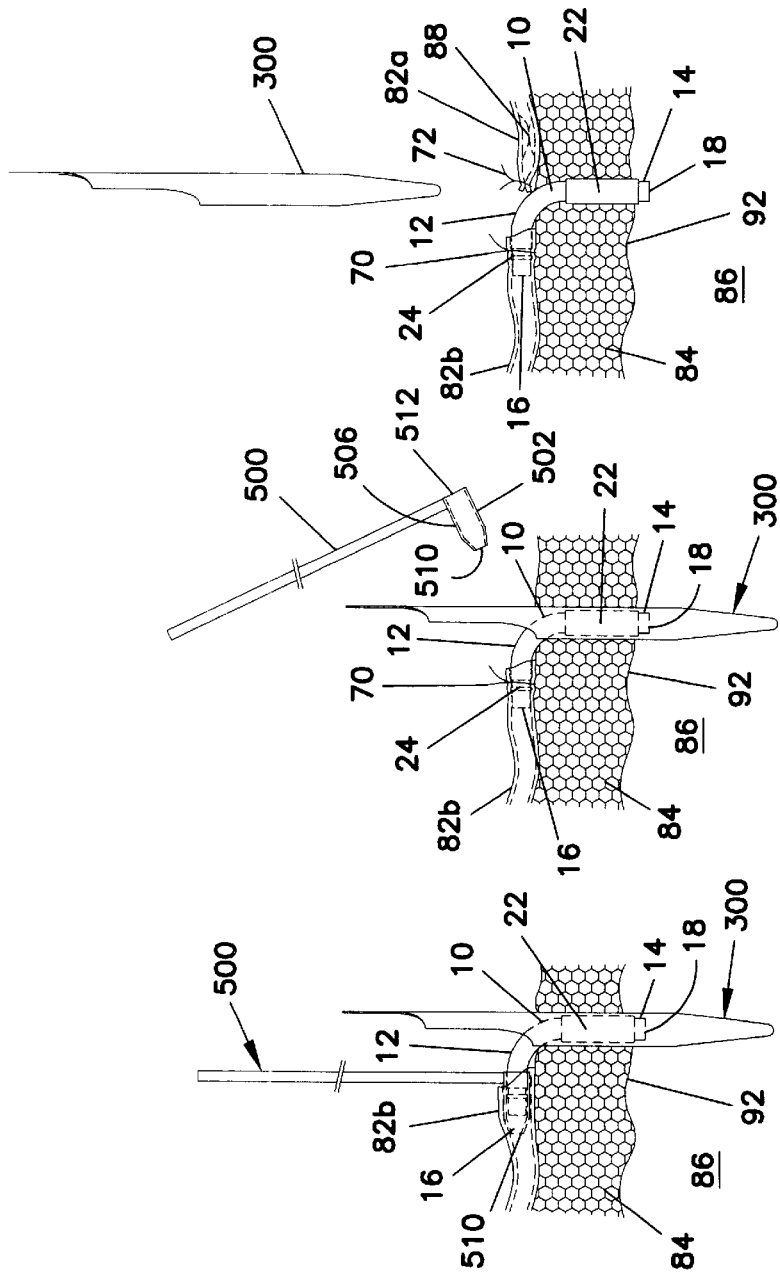
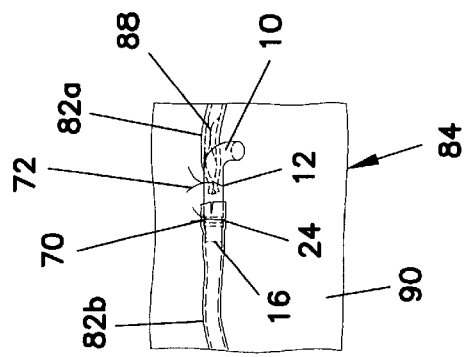

TRANSMYOCARDIAL IMPLANT PROCEDURE

This application is a Continuation of application Ser. No. 09/063,160 now U.S. Pat. No. 6,029,672, filed Apr. 20, 1998, which application(s) are incorporated herein by reference.

I. BACKGROUND OF THE INVENTION

1. Field of the Invention

The present invention pertains to cardiac revascularization and more particularly to a procedure for cardiac revascularization and related tools for forming a blood flow path through a heart wall from a heart chamber to a coronary vessel.

2. Description of the Prior Art

Commonly assigned and co-pending U.S. patent application Ser. No. 08/882,397 filed Jun. 25, 1997 (now issued as U.S. Pat. No. 5,944,019), entitled "Method and Apparatus for Performing Coronary Bypass Surgery", and filed in the name of inventors Mark B. Knudson and William L. Giese, teaches an implant for defining a blood flow conduit directly from a chamber of the heart to a lumen of a coronary vessel. The text of the '397 application has been published on Feb. 25, 1998 in corresponding UK Patent Application GB 2 316 322 A. An embodiment disclosed in the aforementioned application teaches an L-shaped implant in the form of a rigid conduit. The conduit has one leg sized to be received within a lumen of a coronary artery and a second leg sized to pass through the myocardium and extend into the left ventricle of the heart. As disclosed in the above-referenced application, the conduit is rigid and remains open for blood flow to pass through the conduit during both systole and diastole. The conduit penetrates into the left ventricle in order to prevent tissue growth and occlusions over an opening of the conduit.

Commonly assigned and co-pending U.S. patent application Ser. No. 08/944,313 filed Oct. 6, 1997 (now issued as U.S. Pat. No. 5,984,956), entitled "Transmyocardial Implant", and filed in the name of inventors Katherine S. Tweden, Guy P. Vanney and Thomas L. Odland, teaches an implant such as that shown in the aforementioned '397 application with an enhanced fixation structure. One embodiment of the enhanced fixation structure includes a fabric surrounding at least a portion of the conduit to facilitate tissue growth on the exterior of the implant.

Implants such as those shown in the aforementioned applications include a portion to be placed within a coronary vessel and a portion to be placed within the myocardium. When placing an implant in the myocardium, a hole is formed through the heart wall into the left ventricle. As a result, blood may flow out of the left ventricle through the formed hole or through the implant after insertion through the myocardium. In addition to undesirable blood loss, the uncontrolled flow of blood can obscure a surgeon's field of vision.

When placing a portion of the implant in the coronary artery or other coronary vessel, the artery is incised by an amount sufficient to insert the implant. Preferably, the artery is ligated distal to an obstruction. A transverse incision is made through the artery distal to the ligation. Such an incision results in a contraction of the coronary vessel to a size substantially smaller than the implant. Therefore, it is difficult to insert the implant into the lumen of the coronary vessel. Such vessels are elastic and can be urged to an expanded shape sufficient to fit over the implant. However, due to the small size of the vessel, restricted space for manipulating surgical tools, and the importance of avoiding damage to the coronary vessel, such a manipulation of the vessel is difficult. Also, it is desirable to be able to insert the implant within the vessel as rapidly as possible to minimize the amount of time during which blood flow through the vessel is interrupted.

II. SUMMARY OF THE INVENTION

According to a preferred embodiment of the present invention, a method and related tools are disclosed for forming a blood flow path from a heart chamber to a coronary vessel at an exterior surface of a heart wall. The method includes selecting a hollow conduit having a vessel portion and a myocardial portion. The vessel portion has an open leading end sized to be inserted into the coronary vessel. The myocardial portion has an open leading end. The myocardium portion is sized to extend through a thickness of the heart wall. The myocardial portion is placed in the heart wall with the open leading end of the myocardial portion protruding into the heart chamber. Blood flow through the conduit from the heart chamber is at least partially blocked. Blood flow through the conduit from the heart chamber is opened. The leading end of the vessel portion is placed in the coronary vessel. The tools of the invention include sheaths for temporarily surrounding the vessel and myocardial portions of the implant. The sheaths facilitate placement of the implant and are removed over the implant following placement.

III. BRIEF DESCRIPTION OF THE DRAWINGS

FIG. 1 is a side elevation view of an implant for use with the present invention;

FIG. 2 is a side cross-sectional view of the implant of FIG. 1;

FIG. 9A is an end elevation view of a distal tip of the myocardial sheath of FIG. 8;

FIG. 10 is a side elevation view of a myocardial dilator;

FIG. 11 is a side cross-sectional view of the myocardial dilator of FIG. 10;

FIG. 12 is a side cross-sectional view of the myocardial dilator of FIG. 11 containing the guide wire of FIG. 4 and with the myocardial dilator received within the myocardial sheath of FIG. 7;

FIG. 13 is a side elevation view of a coronary vessel sheath;

FIG. 14 is a front elevation view of the coronary vessel sheath of FIG. 13;

FIG. 15 is a side cross-sectional view of the coronary vessel sheath of FIG. 13;

FIG. 21 is a top plan view of FIG. 20 with the guide wire and guide needle shown in transverse cross-section at the heart wall surface;

FIG. 22 is the view of FIG. 20 following removal of the guide needle;

FIG. 23 is a top plan view of FIG. 22 with the guide wire shown in transverse cross-section at the heart wall surface;

FIG. 24 is the view of FIG. 22 showing placement of the myocardial dilator of FIG. 10 and the myocardial sheath of FIG. 18 on the guide wire and before insertion of the myocardial dilator and the myocardial sheath through the myocardium;

FIG. 25 is the view of FIG. 24 following placement of the myocardial dilator and myocardial sheath through the myocardium;

FIG. 26 is a top plan view of FIG. 25 with the guide wire, myocardial dilator and myocardial sheath shown in transverse cross-section at the heart wall surface;

FIG. 27 is the view of FIG. 25 showing removal of the myocardial dilator and guide wire and leaving the myocardial sheath in the myocardium;

FIG. 28 is a top plan view of FIG. 27 with the myocardial sheath shown in transverse cross-section at the heart wall surface;

FIG. 29 is the view of FIG. 27 following complete removal of the myocardial dilator and guide wire and following placement of a myocardium portion of the transmyocardial implant of FIG. 1 within the myocardial sheath;

FIG. 30 is a top plan view of FIG. 29 with the myocardial sheath shown in transverse cross-section at the heart wall surface;

FIG. 31 is the view of FIG. 30 following incision of the artery and ligation of the artery distal to the obstruction;

FIG. 32 is a side sectional view of FIG. 31 (without showing the implant and myocardial sheath) showing initial insertion of the coronary vessel sheath of FIG. 13 into the coronary artery;

FIG. 33 is a side sectional view of FIG. 32 (without showing the implant and myocardial sheath) showing full insertion of the coronary vessel sheath of FIG. 13 into the coronary artery;

FIG. 34 is a top plan view of FIG. 33 showing the implant and with the myocardial sheath shown in transverse cross-section at the heart wall surface;

FIG. 35 is a side sectional view of FIG. 34 showing the implant and myocardial sheath (not shown in cross section) tilted for placement of a vessel portion of the implant within the coronary vessel sheath and, for ease of illustration, not showing a proximal portion of the artery;

FIG. 36 is the view of FIG. 35 following full placement of the vessel portion of the implant within the coronary vessel sheath;

FIG. 37 is the view of FIG. 36 following suture of the artery to the vessel portion of the implant and showing removal of the coronary vessel sheath;

FIG. 38 is the view of FIG. 37 showing removal of the myocardial sheath;

FIG. 39 is a top plan view of the elements of FIG. 38 following complete removal of the myocardial sheath;

IV. DESCRIPTION OF THE PREFERRED EMBODIMENT

Referring now to the several drawing figures, in which identical elements are numbered identically throughout, a description of a preferred embodiment of the present invention will now be provided. Throughout the description, specific dimensions and materials of elements of the invention are given. Such specificity is presented to facilitate an understanding of the invention and is not intended to limit the scope of the claims appended hereto. For example, sizing of the elements is given to illustrate how the elements cooperatively fit together during the procedure of the invention. The procedure is described with reference to placement of a transmyocardial implant 10 between a coronary artery 82 and a left ventricle 86. It will be appreciated the invention is applicable to the formation of a direct blood flow path between a heart chamber (left or right ventricle or atrium) and a coronary vessel (artery or vein). Further, vessel size and myocardium thickness vary throughout the heart. The size of the implant 10 will vary depending upon a vessel selected for a procedure and a myocardium thickness. Accordingly, the recited size of the elements of the invention will also vary to cooperate with the selected size of the implant 10 as will become apparent.

Figure 7:
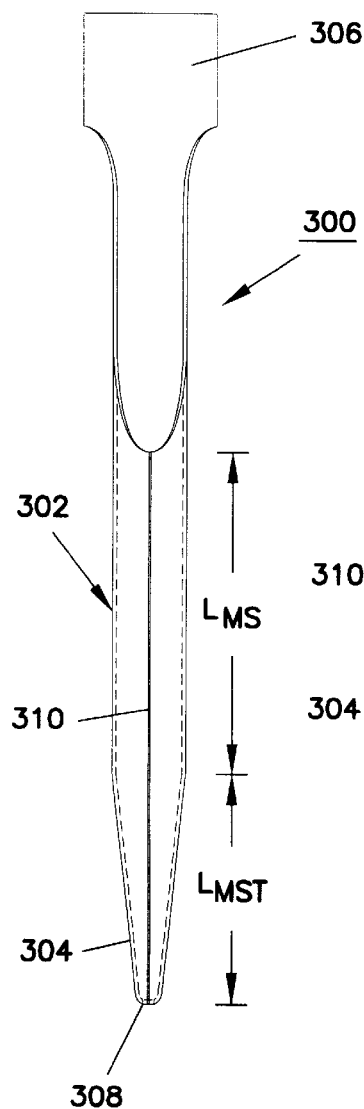
FIG. 7 is a front elevation view of a myocardial sheath.
Figure 8:
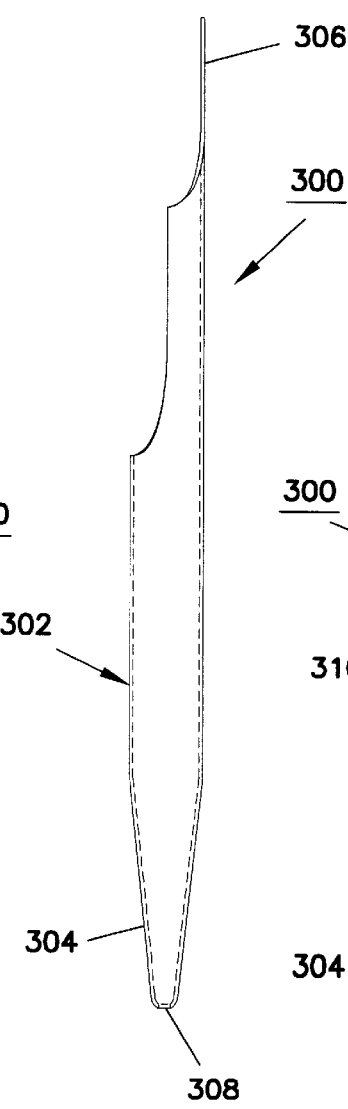
FIG. 8 is a side elevation view of the myocardial sheath of FIG. 7.
Figure 9:
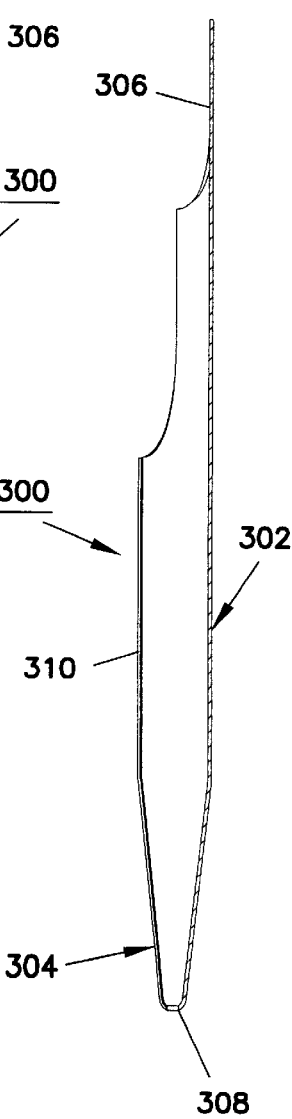
FIG. 9 is a side cross-sectional view of the myocardial sheath of FIG. 8.

The present invention relates to a novel implant procedure using, in part, novel tools for placing an implant 10 (FIGS. 1–2). The tools in the kit include a guide needle 200 (FIGS. 5–6), a guide wire 100 (FIGS. 3–4), a novel myocardial sheath 300 (FIGS. 7–9), a myocardial dilator 400 (FIGS. 10–11) and a novel coronary vessel sheath 500 (FIGS. 13–15). A separate description of the implant 10 and all tools will be followed by a description of the procedure.

A. IMPLANT DESCRIPTION

With initial reference to FIGS. 1 and 2, a conduit 10 is shown in the form of an L-shaped rigid tube. The conduit 10 may be formed of titanium or other rigid biocompatible material such as pyrolytic carbon or may be titanium coated with pyrolytic carbon or other anti-thrombotic material such as parylene. The material of the conduit 10 is preferably a rigid material in order to withstand contraction forces of the myocardium 84. By way of example, the implant 10 will have an outside diameter $D_o$ of about 3 millimeters and an internal diameter $D_I$ of about 2 millimeters to provide a wall thickness of about 0.5 millimeters.

Figure 17:
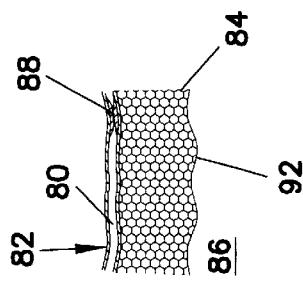
FIG. 17 is a side sectional view of the coronary artery of FIG. 16 showing the artery, obstruction and a myocardium in cross-section.
Figure 16:
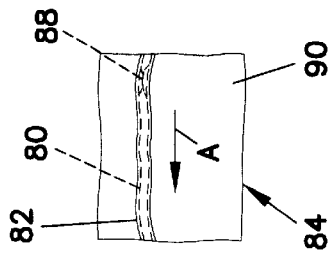
FIG. 16 is a plan view of a coronary artery with an obstruction lying on an outer surface of a heart wall.

The tube 10 has a first portion (or vessel end) 12 which is sized to be received within the lumen of a coronary vessel such as the lumen 80 of a coronary artery 82 (FIGS. 16–17). The conduit 10 has a second portion (or myocardial end) 14 extending at about a right angle to the axis of portion 12. The second portion 14 is sized to extend from the coronary artery 82 directly through the myocardium 84 and into the left ventricle 86 of a patient's heart. The myocardial portion 14 is sized to have a length sufficient for the myocardial portion 14 to protrude into the left ventricle 86.

The vessel end 12 has a first opening 16 and the myocardium end 14 has a second opening 18 in communication with an interior 20 of the implant 10. Therefore, blood can freely flow through the implant 10 between the left ventricle 86 and the lumen 80 of the coronary artery 82. By way of non-limiting example, the implant has a myocardial length ($L_M$) measured from vessel portion 12 to second opening 18 of about 25 mm. The implant 10 has a vessel length ($L_V$) measured from myocardial portion 14 to first opening 16 of about 6 mm.

As illustrated in FIGS. 1 and 2, a sleeve 22 surrounds the myocardial portion 14 and spaced from second opening 18. Preferably, the sleeve 22 is formed of a fabric having biocompatible fibers defining interstitial spaces to receive tissue growth. An example of such a fabric is polyethylene terephthalate (such as polyester fabric sold by DuPont Company under the trademark Dacron). Such a fabric permits rapid tissue integration into the fabric to anchor the fabric and, hence, the implant 10 to the patient's tissue.

The vessel portion 12 is secured in place by means of a reduced-diameter groove 24 formed adjacent the first end 16. With the reduced-diameter groove 24, a surgeon can place sutures 70 (FIG. 37) surrounding the coronary artery 82 to secure coronary artery immobilized at the groove 24 as will be described.

The foregoing description with reference to FIGS. 1 and 2 is provided for illustration and is more thoroughly described in the aforementioned application entitled "Transmyocardial Implant".

B. TOOLS DESCRIPTION

1. Guide Needle

Figure 5:
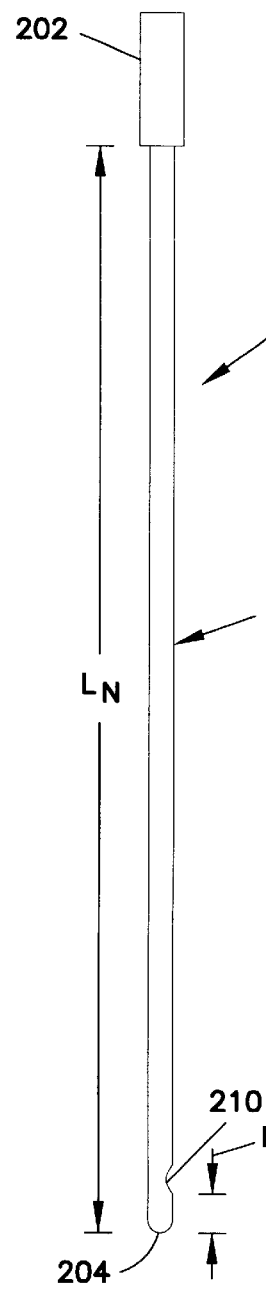
FIG. 5 is a side elevation view of a guide needle for use with the present invention.
Figure 6:
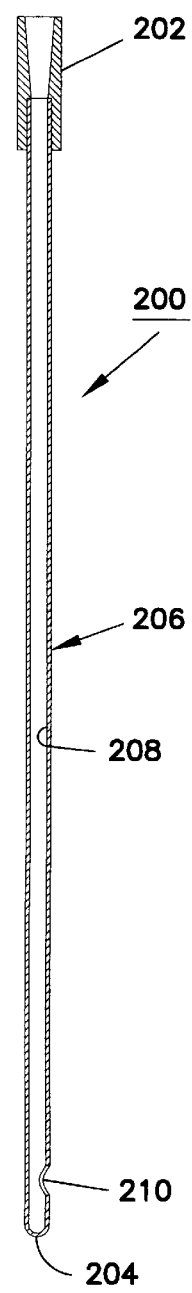
FIG. 6 is a side cross-sectional view of the guide needle of FIG. 5.

Shown separately in FIGS. 5–6, the guide needle 200 is a commercially available item. The needle 200 has a stainless steel construction and has a uniform diameter needle body 206 extending from a handle 202 to a blunt distal tip 204. The needle body 206 has an in outside diameter of 1.8 mm. The distance ($L_N$) from the handle 202 to the tip 204 is 8.8 cm.

The needle 200 has an axially extending bore 208 (1.2 mm diameter) which extends axially through the handle 202 but terminates a distance ($L_T$) of 3.5 mm from the distal tip 204. At such location, the bore 208 has a side-extending portion 210 extending through the side of the needle body 206. The needle body 206 may include gradation markings (not shown) to provide a visual indication of depth of penetration.

2. Guide Wire

Figure 3:
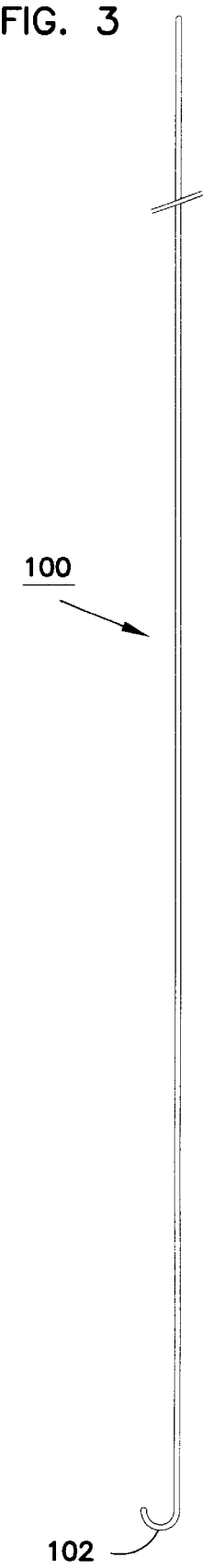
FIG. 3 is a side elevation view of a guide wire for use with the present invention.
Figure 4:
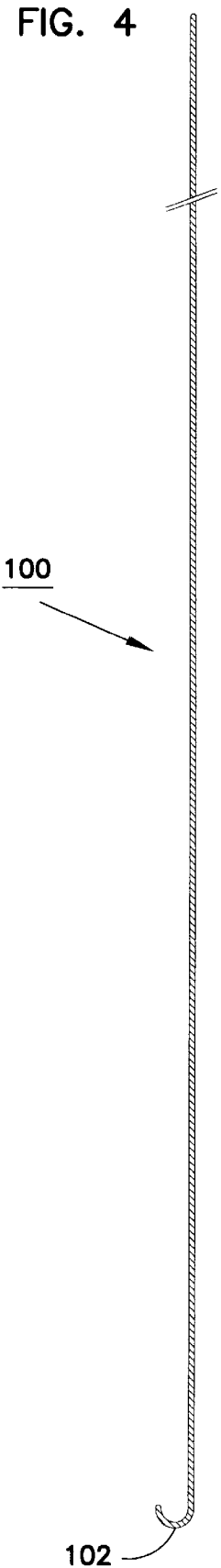
FIG. 4 is a side cross-sectional view of the guide wire of FIG. 3.

Shown separately in FIGS. 3–4, the guide wire 100 has a uniform outside diameter of 0.9 mm along its length for the wire 100 to be slidably received within the bore 208 of the needle 200. Preferably, the wire 100 is formed of a coil construction customary in catheter guide wire construction. Such a construction permits the distal tip 102 of the guide wire 100 to be pre-bent as illustrated in FIGS. 3–4. The coil construction results in the bent end 102 being easily straightened but resilient to be biased to the bent shape. Accordingly, as the guide wire 100 is advanced through the guide needle 200, the bent tip 102 is biased to extend through the hole 210 in the side of the needle 200.

3. Myocardial Sheath

Shown separately in FIGS. 7–9 and 9A, the myocardial sheath 300 has a plastic (e.g., polytetrafluoroethylene) hollow cylindrical body 302 terminating at a hollow conical distal tip 304. The body 302 has an attached proximal handle 306 to permit grasping by a surgeon.

The cylindrical body 302 has an axial length ($L_{MS}$) of 35.6 mm and an outer diameter ($D_{MS}$) of 4.9 mm. The conical tip 304 has an axial length ($L_{MST}$) of 13 mm. The apex of the tip 304 can be closed (not shown) or, more preferably, provided with a through-hole 308 (shown best in FIG. 9A) equal in size to the diameter of the guide wire 100.

The material of the body 302 and tip 304 has a wall thickness of 0.25 mm. The inside diameter of the body 302 is slightly less than the outside diameter of the sleeve 22 of the implant 10. Therefore, after placement of the myocardial portion 14 of the implant 10 within the myocardial sheath 300, as will be described, the sleeve 22 acts as a gasket to seal against the interior surface of the body 302 to prevent blood flow between the sheath 300 and the implant 10.

The body 302 and tip 304 have an axially extending part-line 310 on a side of the body 302 opposite handle 306. The part-line 310 may be a score partially or totally through the wall thickness or perforations through the wall thickness. The part-line 310 permits the sheath 300 to be split open along its axial length. The body 302 and tip 304 are flexible to spread apart at the part-line 310 by a separation sufficient to pass the sheath 300 over the implant 10 as will be described.

4. Myocardial Dilator

Shown separately in FIGS. 10–11, the myocardial dilator 400 is a commercially available item. The dilator 400 is plastic construction having a constant diameter body 402 extending between a proximal handle 404 and a tapered conical distal tip 406. The dilator 400 is sufficiently stiff to permit the dilator 400 to be urged through the myocardium 84 without deformation of the dilator 400.

The body 402 of the dilator is cylindrical with a 4.1 mm outer diameter (i.e., approximate to the interior diameter of the body 302 of the myocardial sheath 300). The dilator body 402 has a length ($L_D$) of 191 mm and the conical tip 406 has a length ($L_{DT}$) of 12.7 mm. The external geometry of the cylindrical body 402 and conical tip 406 are complementary to the internal geometry of the myocardial sheath 300 for the dilator 400 to be received within the sheath 300 as illustrated in FIG. 12. The dilator 400 is hollow to present an internal bore 408 extending axially through both the handle 404 and the distal tip 406. The bore 408 is sized to pass the guide wire 100 as shown in FIG. 12.

5. Coronary Vessel Sheath

Shown separately in FIGS. 13–15, the coronary vessel sheath 500 includes a sheath body 502 secured to a handle 504. The sheath body 502 includes a cylindrical portion 506 and a tapered frusto-conical portion 508. The handle 504 extends radially away from a side of the cylindrical portion 506 at an axial end of the cylindrical portion 506.

The cylindrical portion 506 and the tapered portion 508 are molded from a flexible material such as polyethylene. The cylindrical portion 506 has an outer diameter of 3.7 mm and an axial length ($L_{VS}$) of 5 mm. The tapered portion 508 has an axial length ($L_{VST}$) of 3.5 mm and an outer diameter ($D_{VST}$) of 1.0 mm at a leading end 510. Both of the cylindrical portion 506 and the tapered portion 508 have a wall thickness of 0.25 mm and have an open leading 510 and an open trailing end 512.

Both of the cylindrical portion 506 and the tapered portion 508 have an axially extending part-line 514 on a side of the sheath body 502 opposite the handle 504. The part-line 514 may be a score partially or totally through the wall thickness or perforations through the wall thickness. The part-line 514 permits the sheath body 502 to be split open along its axial length.

The trailing end axial opening 512 has an internal diameter of 3.2 mm to permit insertion of the first end 16 of the vessel portion 12 of the implant 10. The outer diameter ($D_{VST}$) of the leading end 510 is sized for ease of insertion into an incised coronary vessel 82.

C. PROCEDURE

The procedure of the present invention is illustrated in FIGS. 16–39. FIG. 16 is a plan view of an exterior surface 90 of a heart wall 84 with a coronary vessel 82 lying on the surface 90. A lumen 80 of the vessel 82 is shown in phantom lines. The present procedure and tools are applicable for use in a wide number of coronary vessels. For ease of discussion, the invention will be described with reference to vessel 82 being a coronary artery (e.g., LAD) on the left side of the heart overlying a left ventricle 86. Normal blood flow through the artery 82 is in the direction of arrow A. Such blood flow is at least partially obstructed by an occlusion 88. FIG. 17 is a cross-sectional view of FIG. 16 showing the interior surface 92 of the heart wall (i.e., myocardium 84) and the left ventricle 86.

In one method of placing the vessel end 12 into the artery 82, an incision is made along a length of an upper surface of the artery 82. The portion of the artery 82 proximal to the incision is closed by sutures.

The process of incising the artery 82 results in contraction of the artery 82 to a reduced diameter. For example, an artery 82 such as the left anterior descending artery (LAD) may contract down to 0.5 mm. This is smaller than the diameter of the leading end 16 of the implant 10. The artery 82 is elastic and may be expanded to an enlarged expanded diameter (e.g., 4–5 mm). However, it is difficult to manipulate tools to expand the artery 82 due to the limited space available in which to work. Further, such manipulation can be time-consuming and it is desirable to reduce the amount of time that blood flow through the artery 82 is interrupted. Also, it may be desirable to first place the myocardium portion 14 of the implant 10 through the myocardium 84 before inserting the vessel portion 12 of the implant 10 into the artery 82. In beating heart operations, such a sequence of procedures can result in blood ejecting from opening 16 of the implant 10. This would obscure vision and otherwise makes the insertion procedure more difficult.

The method of the present invention utilizes the above-described tools of the invention to place an implant 10 rapidly with minimal blood loss and with reduced likelihood of damage to the coronary vessel 82.

1. Placement of Implant in Myocardium a. Measurement of Myocardial Thickness

Figure 19:
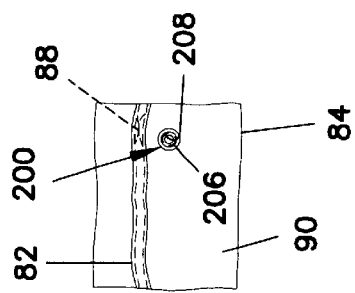
FIG. 19 is a top plan view of FIG. 18 (and showing the coronary obstruction) with the guide needle shown in transverse cross-section at the heart wall surface.
Figure 18:
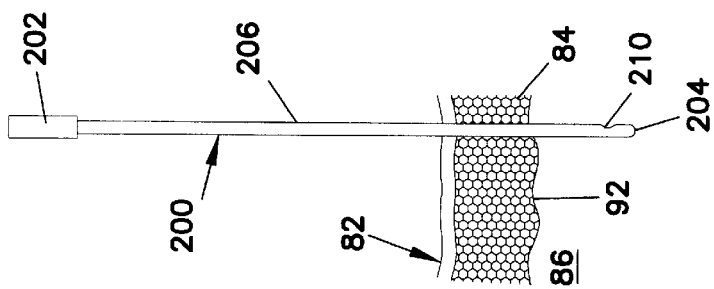
FIG. 18 is the view of FIG. 17 following placement of a guide needle of FIG. 5 with the guide needle not shown in cross-section and with the coronary obstruction not shown for ease of illustration.

A surgeon places the distal tip 204 of guide needle 200 through the myocardium 84 at a location about 3.5 mm transverse to the axis of the artery 82 (FIGS. 18–19). When the side opening 210 of the needle 200 passes the inner surface 92 of the myocardium 84, blood flow through the needle 200 indicates the needle 200 has penetrated into the left ventricle 86. By observing external gradation marks (not shown) on the needle 200, the surgeon can confirm the thickness of the myocardium 84 and select an implant 10 with a myocardial portion 14 of sufficient length to penetrate into the left ventricle 86 following completion of the procedure. The size of the artery 82 is observed to select an implant 10 of adequate diameter for the vessel portion 12 of the implant 10 to be placed in the artery 82.

Figure 40:
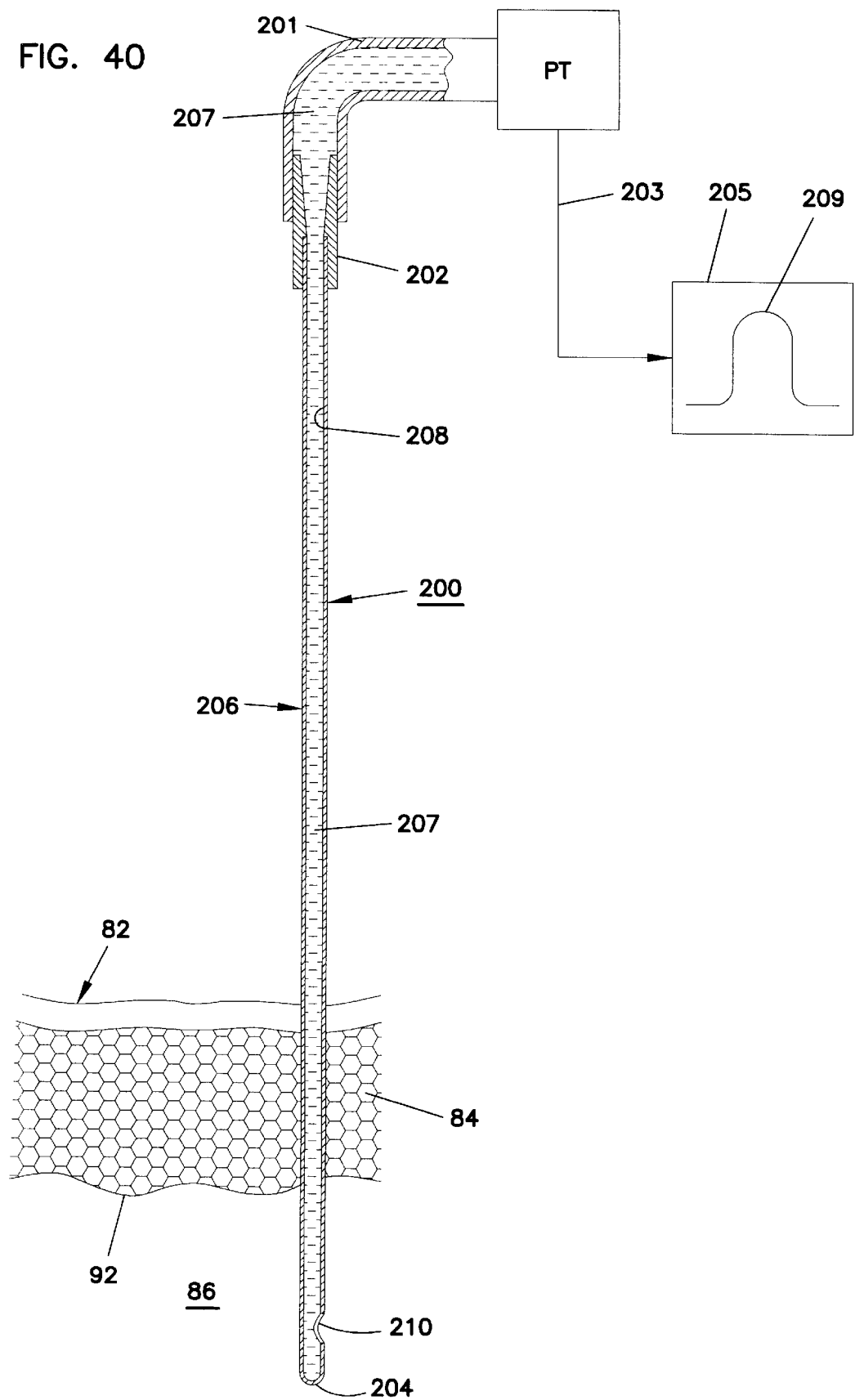
FIG. 40 is a side sectional schematic view showing an alternative procedure for measuring a myocardium thickness.
Figure 41:
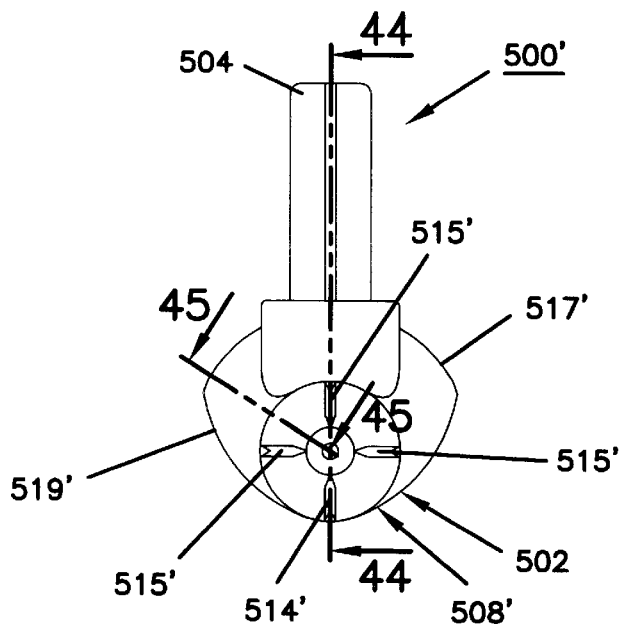
FIG. 41 is a front elevation view of an alternative embodiment of a vessel sheath.
Figure 42:
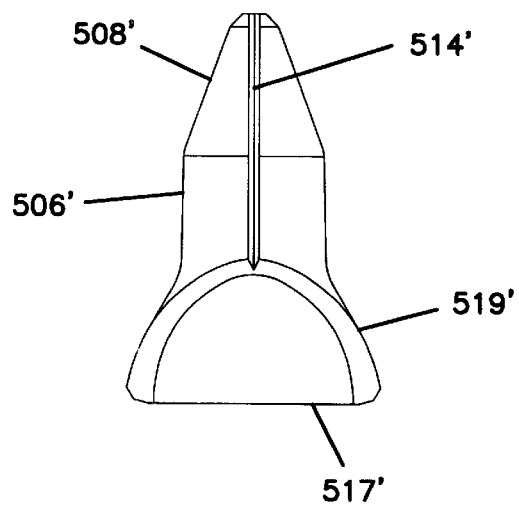
FIG. 42 is a bottom plan view of the sheath of FIG. 41.
Figure 43:
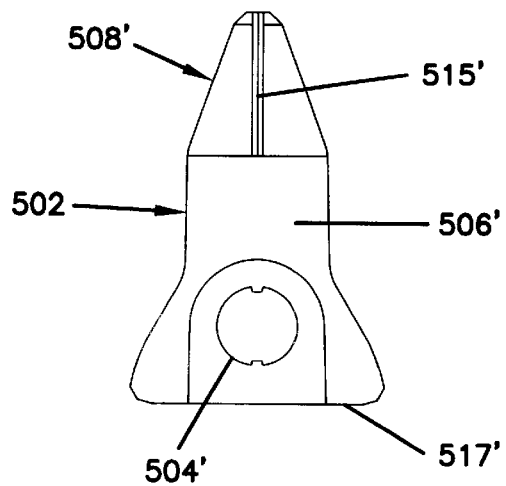
FIG. 43 is a top plan view of the sheath of FIG. 41.
Figure 44:
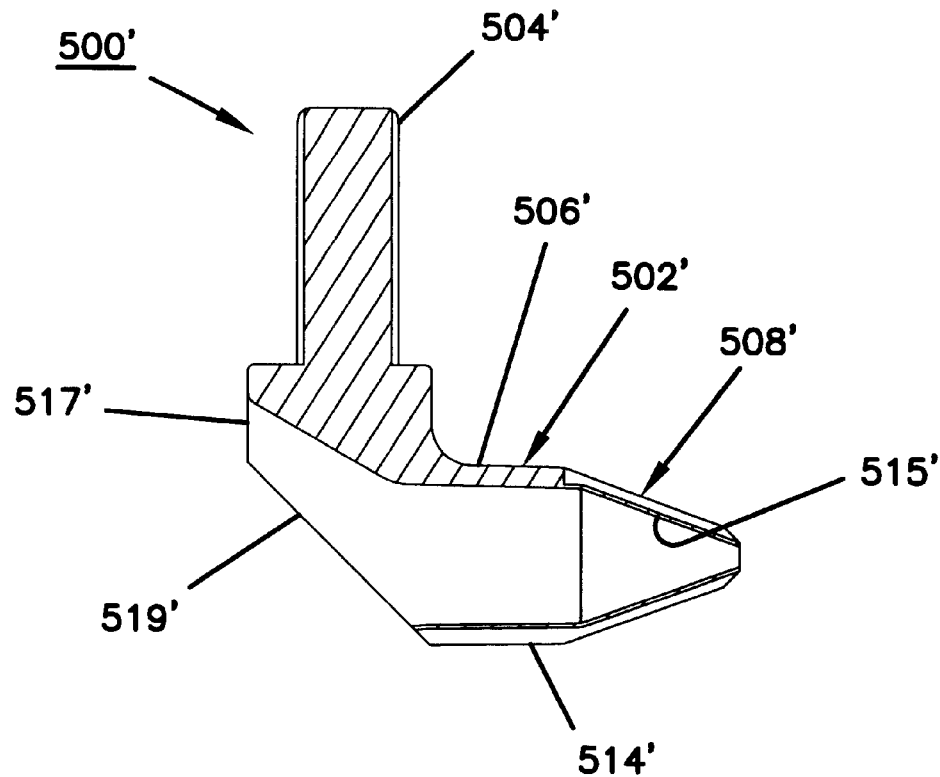
FIG. 44 is a view taken along line 44—44 in FIG. 41.
Figure 45:
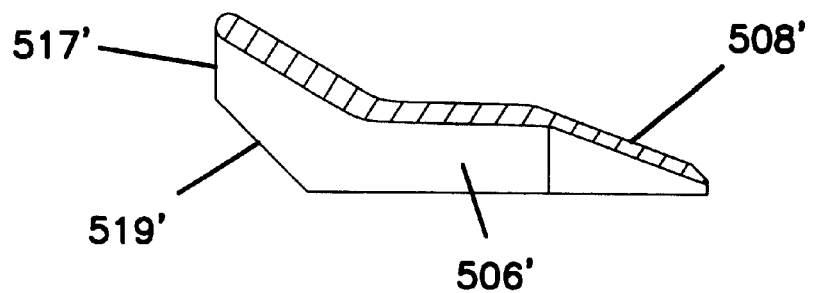
FIG. 45 is a view taken along line 45—45 in FIG. 41.

FIG. 40 illustrates an alternative tool and method for measuring myocardial thickness. In FIG. 40, the needle 200 is fitted with a hollow, flexible tube 201 at proximal end 202. An opposite end of the tube 201 is fitted to a pressure transducer PT. The pressure transducer PT is connected across a signal path 203 to a visual output 205 (such as a CRT). It will be appreciated that pressure transducers PT, visual outputs 205, signal paths 203 and connection of fluid filled tubes 201 to transducers PT are all well-known and hence shown schematically for purpose of ease of illustration.

The tube 201 and needle 200 are filled will a liquid 207 (preferably a saline solution). Since needle 200 is only open at opening 210, the liquid 207 is retained in the tube 201 and needle 200. When the needle 200 is passed through the myocardium 84, the opening 210 permits the liquid 207 to be subject to pressure variations in the left ventricle 86. The pressure variations are transferred by the liquid 207 to the pressure transducer PT. The pressure transducer PT generates a signal in response to the pressure variations and transmits the signal across path 203 to output 205. At output 205, a visual signal 209 is generated representing the pressure in the left ventricle 86 and advising the surgeon the opening 210 has penetrated into the left ventricle 86.

b. Placement of Myocardial Sheath

Figure 20:
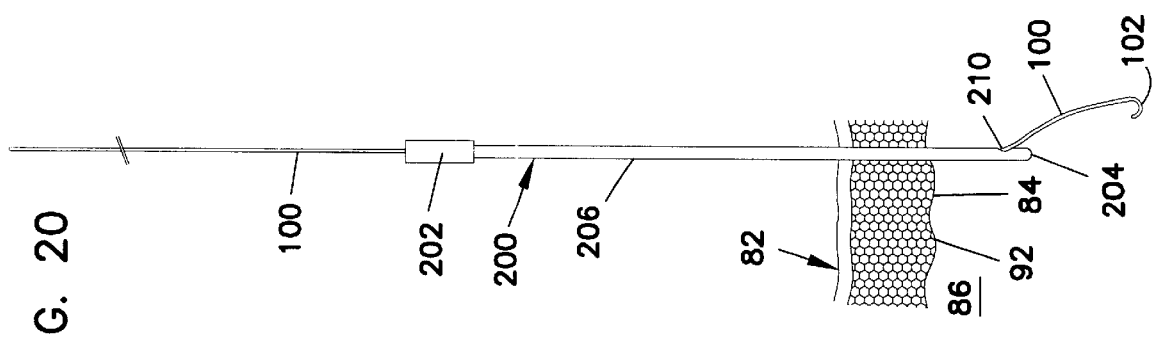
FIG. 20 is the view of FIG. 18 following placement of a guide wire through the guide needle.

The guide wire 100 is passed through the needle 200 by straightening the tip 102 and inserting the tip 102 into the bore 208 through the handle 202 of the needle 200. As the guide wire 100 is passed through the needle 200, the resiliently biased tip 102 is urged out of the needle's side opening 210 (FIGS. 20–21). The guide needle 200 is then removed over the guide wire 100 leaving only the guide wire 100 extending through the thickness of the myocardium 84 (FIGS. 22–23).

The distal tip 406 of the dilator 400 is placed within the conical tip 304 of the myocardial sheath 300. The hole 308 at the tip 304 of the sheath 300 and the bore 408 of the dilator 400 are passed over the guide wire 100 (FIG. 24). With the guide wire 100 insuring desired positioning, the combined myocardial sheath 300 and dilator 400 are urged through the myocardium 84 (FIGS. 25–26). The combined myocardial sheath 300 and dilator 400 urge the tissue of the myocardium 84 apart to form an opening through the myocardium 84 sufficient to pass the myocardial portion 14 of the implant 10. The stiff dilator 400 prevents deformation to the myocardial sheath 300. The sheath 300 is positioned with its part-line 310 facing distally from the obstruction.

The dilator 400 and guide wire 100 are removed leaving only the myocardial sheath 300 extending through the myocardium 84 (FIGS. 27–28). Since the distal tip 304 of the myocardial sheath 300 has a through-hole 308, blood will pass from the left ventricle 86 into the myocardial sheath 300 indicating to the surgeon that the sheath 300 is properly extending into the left ventricle 86. The small diameter through-hole 308 restricts blood flow so that only a small amount of blood enters the sheath 300 so as to avoid obstruction to the surgeon's field of vision. In the event a small amount of blood flow is not desired, the through-hole 308 can be provided with a resilient flap (not shown) so that the through-hole 308 closes when the guide wire 100 is removed.

c. Placement of Implant in Myocardial Sheath

The myocardial portion 14 of the implant 10 is placed within the myocardial sheath 300 (FIGS. 29–30). The outside diameter of the fabric sleeve 22 closely matches the internal diameter of the sheath body 302. Therefore, the implant 10 is snugly received within the sheath 300. As a result, any blood which might flow through the through-hole 308 will flow into the implant 10 and not around the outside of the implant 10. Although not shown, a clamped transparent tube could be connected to the first end 16 of the vessel portion 12 of the implant 10. Such a tube prevents blood loss through the implant 10 and permits the implant 10 to be primed with blood prior to placement of the vessel portion 12 of the implant 10 in the artery 82.

The present invention is illustrated with the myocardial sheath 300 left in place until the end of the procedure as will be discussed with reference to FIG. 38. In the event a clamped tube is used as discussed above, the myocardial sheath 300 can be removed at this point in the procedure.

2. Placement of Implant In Artery a. Ligation and Incision of Artery

The artery 82 is ligated with sutures 72 distal to the obstruction 88 and transversely incised at an incision 74 distal to the ligation (FIG. 31). The incision 74 separates the artery 82 into a proximal portion 82a and a distal portion 82b. The distal portion 82b presents an arterial opening 83 at the incision 74.

In the figures, the incision 74 is shown extending transverse to the artery 82 and completely through the artery 82. Such an incision 74 is shown for ease of illustration. In practice, the surgeon may elect to form incision 74 only partly through (e.g., 50%) the artery 82 and further forming a longitudinal incision on the top of the distal portion 82b of the artery 82 to provide a flap-opening to the distal portion 82b of the artery 82.\ b. Placement of Vessel Sheath in Artery

The leading end 510 of the vessel sheath 500 is placed within the incised opening 83 of the distal portion 82b of the artery 82 (FIG. 32). Due to the taper 508 of the vessel sheath 500, the vessel sheath 500 can be placed in a small diameter artery 82 and urged into the artery 82 with the artery 82 dilated over the cylindrical body 506 of the vessel sheath 500 (FIGS. 33–34). The part-line 514 faces the floor of the artery 82.

Although not shown, a rigid dilator could be used to assist placement of the vessel sheath 500. Similar to myocardial dilator 400, such a vessel dilator would have a rigid tapered plastic tip secured to a handle. The tip would be passed through the sheath body 502 with the tip protruding beyond the open leading end 510 of the sheath 500. Preferably, the outer diameter of the vessel dilator will closely conform to the inner diameter of the vessel sheath body 502 to provide structural support of the sheath body 502. The protruding tapered tip of the dilator is smaller in diameter than the sheath end 510 thereby facilitating placing in a small artery. The vessel dilator is removed following placement of the vessel sheath 500.

c. Placement of Implant in Vessel Sheath

With the vessel sheath 500 fully inserted into the artery 82, the implant 10 and myocardial sheath 300 can be manipulated to align the open end 16 of the vessel portion 12 of the implant 10 with the open trailing end 512 of the vessel sheath 500. Since the myocardium 84 is a pliable tissue, the implant 10 and myocardial sheath 300 can easily be manipulated (such as tilted) to effect such alignment (FIG. 35). Since the myocardial sheath 300 is very flexible, such manipulation is preferably performed with a rigid tool (e.g., a releasable clamp) secured to the vessel portion 12 of the implant 10.

The open end 16 of the vessel portion 12 of the implant 10 is passed through the open trailing end 512 of the vessel sheath 500. The vessel portion 12 is advanced into the vessel sheath body 502 at least as far as the start of the tapered portion 508 of the vessel sheath 500 (FIG. 36).

In the event a clamped tube has been placed on the open end 16 of the vessel portion 12 of the implant 10 (as previously described), the tube is removed prior to insertion of the vessel portion 12 into the vessel sheath 500. The removal of the tube results in blood flowing out of the implant 10. The open trailing end 512 of the vessel sheath 500 presents a large target area for a surgeon and avoids a surgeon being unable to place the implant 10 due to visual obstruction resulting from such blood flow.

The open leading end 510 of the vessel sheath 500 permits blood flow from the implant 10 into the artery 82 immediately upon placement of the implant 10 in the vessel sheath 500. Therefore, flow of blood continues through the artery 82 while the remainder of the procedure is taking place. Blood flow distal to the obstruction 88 is interrupted for only a short period following the ligation and incision of the artery 82 since the vessel sheath 500 can be placed quickly.

FIGS. 41–45 illustrate an alternative vessel sheath 500' to facilitate placement of the implant end 16 into the sheath 500'. Elements in common between sheath 500' and sheath 500 are numbered identically with the addition of an apostrophe to distinguish the embodiments. Such elements are not separately described.

The tapered leading end 508' of sheath 500' has a score line 514' partially cut through the tapered end 508' and cylindrical body 506' serving the purpose of part-line 514 of sheath 500. Additionally, score lines 515' are partially cut through the tapered leading end 508'. The score lines 515' are placed at 90° intervals about the axis of the tapered end 508'. So cut, the tapered leading end 508' flares open during removal. The trailing end 512' is provided with an enlarged cone 517' to act as a funnel to guide the implant into the cylindrical body 506'. The cone 517' is open at the bottom (illustrated by bevel cut 519') so a surgeon can easily place the implant within the cone 517'.

d. Removal of Vessel and Myocardial Sheaths

The artery 82 is secured to the vessel portion 12 of the implant by sutures 70 surrounding the artery 82 in overlying relation to the groove 24 (FIG. 37). The surgeon grasps the handle 504 of the vessel sheath 500 and pulls the sheath body 502 over the implant 10. The vessel sheath body 502 splits open at its part-line 514 and the wall of the vessel sheath body 502 flexes open to permit the sheath body 502 to clear the implant 10 leaving only the vessel portion 12 of the implant 10 within the artery 82. Sutures 70 are placed following removal of the vessel sheath 500. The removal of the vessel sheath body 502 further acts to draw the artery 82 over the vessel portion 12 of the implant 10.

The surgeon grasps the handle 306 of the myocardial sheath 300 and pulls the sheath 300 out of the myocardium 84 (FIGS. 38–39). The myocardial sheath 300 splits open at its part-line 310 and the wall of the myocardial sheath 300 flexes open to permit the sheath 300 to clear the implant 10 leaving only the myocardial portion 14 and sleeve 22 of the implant 10 within the myocardium 84. Since the myocardial portion 14 is placed in a hole in the myocardium 84 formed by the dilator 400, the tissue of the myocardium 84 is biased to urge against the implant 10 holding it in place. Subsequent tissue growth into the sleeve 22 further secures the implant 10 within the myocardium.

In the foregoing description, the invention has been shown in a preferred embodiment. The invention permits quick placement of the implant 10 while minimizing time during which blood is not flowing through the artery 82. The method and tools reduce uncontrolled blood flow which would otherwise obscure a surgeon's vision and reduce likelihood of damage to the artery 82. Modifications and equivalents of the disclosed concepts are intended to be included within the scope of the claims.

What is claimed is:

1. A method for forming a blood flow path from a heart chamber to a coronary vessel at an exterior surface of a heart wall, the method comprising:

selecting a hollow conduit having a vessel portion and a myocardial portion, the vessel portion having an open leading end and the myocardial portion having an open leading end, the myocardium portion being sized to extend through a thickness of the heart wall;

placing the myocardial portion in the heart wall with the open leading end of the myocardial portion protruding into the heart chamber while at least partially blocking flow of blood through the conduit from the heart chamber;

connecting the leading end of the vessel portion to the coronary vessel;

opening blood flow through the conduit from the heart chamber and into the vessel;

wherein the placing of the myocardial portion includes:

placing a myocardial sheath in the heart wall with the myocardial portion of said hollow conduit placed within the myocardial sheath and with the myocardial sheath and myocardial portion extending through the thickness of the heart wall; and removing the myocardial sheath while leaving the myocardial portion of said hollow conduit within the heart wall.

2. A method according to claim 1 wherein the blocking of the blood flow is provided by the myocardial sheath at least partially covering the leading end of the myocardial portion of said hollow conduit.

3. A method according to claim 2 wherein the myocardial sheath is configured to substantially surround the myocardial portion of said hollow conduit and the myocardial sheath includes a part line along a length of the myocardial sheath, the removing of the myocardial sheath including retracting the myocardial sheath by urging the myocardial sheath out of the heart wall with the myocardial sheath separating at the part line to clear the conduit.

4. A method according to claim 1 wherein the myocardial sheath and myocardial portion of said hollow conduit are placed in the heart wall by first placing the myocardial sheath in the heart wall and extending into the heart chamber and subsequently placing the myocardial portion into the myocardial sheath.

5. A method according to claim 4 wherein the myocardial sheath is placed in the heart wall by placing a dilator in the myocardial sheath and advancing the myocardial sheath and dilator into the heart wall for the myocardial sheath to penetrate into the heart chamber and subsequently removing the dilator.

6. A method according to claim 1 wherein said uncovering of said open leading end of the myocardial portion of the hollow conduit occurs before the connecting of the leading end of the vessel portion to the coronary vessel.

7. A method according to claim 1 wherein the leading end of the vessel portion is sized to be inserted into the coronary vessel, and the connecting of the leading end of the vessel portion to the coronary vessel includes:

placing a vessel sheath in the coronary vessel with the sheath having an opening sized to receive the leading end of the vessel portion of said hollow conduit;

placing the leading end of the vessel portion of said hollow conduit within the vessel sheath; and removing the vessel sheath while leaving the leading end of the vessel portion of said hollow conduit within the coronary vessel.

8. A method according to claim 7 wherein the vessel sheath has a main portion sized to receive the leading end of the vessel portion of said hollow conduit and the vessel sheath has a leading end smaller than the main portion, the placing of the vessel sheath including placing the leading end of the vessel sheath into the coronary vessel and advancing the vessel sheath into the coronary vessel to dilate the coronary vessel as the main portion of the vessel sheath is advanced into the coronary vessel.

9. A method according to claim 7 wherein the vessel sheath is configured to substantially surround the leading end of the vessel portion of said hollow conduit when the vessel portion of said hollow conduit is inserted into the vessel sheath and the vessel sheath includes a part line along a length of the vessel sheath, the removing of the vessel sheath including retracting the vessel sheath by urging the vessel sheath out of the vessel and away from the vessel portion with the vessel sheath separating at the part line to clear the vessel portion.

10. A method according to claim 1 wherein said opening of blood flow occurs before the connecting of the leading end of the vessel portion to the coronary vessel.

11. A method for forming a blood flow path from a heart chamber to a coronary vessel at an exterior surface of a heart wall, the method comprising:

providing a hollow conduit having a vessel portion and a myocardial portion;

placing the myocardial portion through the heart wall while at least partially blocking flow of blood through the conduit from the heart chamber;

connecting the vessel portion of the conduit to the coronary vessel; opening blood flow through the conduit from the heart chamber and into the vessel; wherein the placing of the myocardial portion includes:

placing a myocardial sheath in the heart wall with the myocardial portion of said hollow conduit placed within the myocardial sheath and with the myocardial sheath and myocardial portion extending through a thickness of the heart wall; and removing the myocardial sheath while leaving the myocardial portion of said hollow conduit within the heart wall.

12. A method for forming a blood flow path from a heart chamber through a heart wall, the method comprising:

providing a hollow conduit having a myocardial portion;

placing the myocardial portion through the heart wall by:

placing a myocardial sheath in the heart wall with the myocardial portion of said hollow conduit placed within the myocardial sheath and with the myocardial sheath and myocardial portion extending through a thickness of the heart wall; and removing the myocardial sheath while leaving the myocardial portion of said hollow conduit within the heart wall by urging the myocardial sheath out of the heart wall and by splitting the myocardial sheath along its length to clear the hollow conduit.

13. The method of claim 12, wherein the myocardial sheath is split by tearing the sheath along a part line.

14. The method of claim 12, wherein when the myocardial portion is being placed in the heart wall, the myocardial sheath at least partially blocks blood flow through the conduit.

15. A method for inserting a conduit into a vessel, the method comprising:

providing a hollow conduit having a vessel portion;

placing the vessel portion into the vessel by:

placing a sheath in the vessel with the vessel portion of said hollow conduit placed within the sheath; and removing the sheath while leaving the vessel portion of said hollow conduit within the vessel by urging the sheath out of the vessel and by splitting the sheath along its length to clear the hollow conduit.

16. The method of claim 15, wherein the sheath is split by tearing the sheath along a part line.

17. The method of claim 15, wherein when the vessel portion is being placed in the vessel, the sheath at least partially blocks fluid flow through the conduit.

* * * * *

UNITED STATES PATENT AND TRADEMARK OFFICE
CERTIFICATE OF CORRECTION

PATENT NO. : 6,237,607 B1
DATED : May 29, 2001
INVENTOR(S) : Vanney et al.

It is certified that error appears in the above-identified patent and that said Letters Patent is hereby corrected as shown below:

<u>Title page,</u>
Item [56], References Cited, OTHER PUBLICATIONS, insert -- Product Brochure, "Ordering Information," *Medcomp*, CAT-014.PM5 (May 1997) --

Signed and Sealed this

Nineteenth Day of August, 2003

JAMES E. ROGAN
*Director of the United States Patent and Trademark Office*